(12) United States Patent
Chan et al.

(10) Patent No.: US 11,409,980 B2
(45) Date of Patent: Aug. 9, 2022

(54) AUDIO-EFFECT-ACTIVATED SCENT GENERATION METHOD AND SYSTEM

(71) Applicant: Acoustic Arc International Limited, Hong Kong (CN)

(72) Inventors: Ho-Yin Chan, Hong Kong (CN); Ka Wai Kong, Hong Kong (CN); Junhui Law, Hong Kong (CN); Meng Chen, Hong Kong (CN); Wen Jung Li, Hong Kong (CN); Boa Fung Chau, Hong Kong (CN); Kak Man Chan, Hong Kong (CN)

(73) Assignee: Acoustic Arc International Limited, Hong Kong (CN)

( * ) Notice: Subject to any disclaimer, the term of this patent is extended or adjusted under 35 U.S.C. 154(b) by 903 days.

(21) Appl. No.: 16/224,894

(22) Filed: Dec. 19, 2018

(65) Prior Publication Data
US 2020/0202102 A1 Jun. 25, 2020

(51) Int. Cl.
*G06F 16/00* (2019.01)
*G06K 9/00* (2022.01)
(Continued)

(52) U.S. Cl.
CPC ............ *G06K 9/0053* (2013.01); *A61L 9/125* (2013.01); *A61L 9/14* (2013.01); *G06F 16/9014* (2019.01);
(Continued)

(58) Field of Classification Search
CPC ... G06K 9/0053; B05B 17/04; G06F 16/9014; G06F 16/90335; G06F 16/9038;
(Continued)

(56) References Cited

U.S. PATENT DOCUMENTS 6,453,252 B1  9/2002  Laroche
8,295,529 B2  10/2012 Petersen
(Continued)

FOREIGN PATENT DOCUMENTS

JP         2005006037 A  *  1/2005  ........... H04L 65/607

*Primary Examiner* — Syed H Hasan
(74) *Attorney, Agent, or Firm* — Spruson & Ferguson (Hong Kong) Limited (57) ABSTRACT

Time-varying scent determined by audio-meaningful events, such as gun firing, in an audio signal is generated by first computing a spectrogram thereof. A fingerprint, each having feature points, can be extracted from the spectrogram over a time window. The plurality of feature points is hashed to give a hash code. A sequence of hash codes obtained over multiple time windows is correlated with predetermined hash-code segments of known audio-meaningful events stored in a database. A matched audio-meaningful event having a highest correlation is identified. The scent-generating recipe corresponding to the matched audio-meaningful event is retrieved. Atomizers are used to vaporize scent-generating substances to generate the time-variant scent. Since the hash code has a fixed length and a smaller size than the plurality of feature points, storage requirements of the database and computation requirements of correlation calculation are reduced by using the hash code rather than the plurality of feature points.

18 Claims, 7 Drawing Sheets

(51) Int. Cl.
  *G06F 16/9038* (2019.01)
  *G06F 16/903* (2019.01)
  *G06F 16/901* (2019.01)
  *A61L 9/12* (2006.01)
  *A61L 9/14* (2006.01)
(52) U.S. Cl.
  CPC .... *G06F 16/9038* (2019.01); *G06F 16/90335* (2019.01); *A61L 2209/111* (2013.01)
(58) Field of Classification Search
  CPC .......... G06F 16/683; A61L 9/125; A61L 9/14; A61L 2209/111
  See application file for complete search history.

(56) References Cited

U.S. PATENT DOCUMENTS

| | | | |
|---|---|---|---|
| 8,976,040 B2* | 3/2015 | Ray Avalani | G06V 20/58 348/148 |
| 9,669,364 B2 | 6/2017 | Chan | |
| 2003/0164557 A1* | 9/2003 | Chung | A61L 9/122 261/26 |
| 2004/0252726 A1* | 12/2004 | Matsumoto | H04N 21/235 370/503 |
| 2005/0195367 A1* | 9/2005 | Selander | A61L 9/125 352/85 |
| 2010/0270388 A1* | 10/2010 | Liu | G06F 3/011 239/289 |
| 2011/0268605 A1 | 11/2011 | Haran | |
| 2012/0173664 A1* | 7/2012 | Kammerer | H04L 51/00 709/217 |
| 2013/0190556 A1* | 7/2013 | Wetmore | A61M 21/00 600/27 |
| 2013/0194437 A1 | 8/2013 | Osman | |
| 2015/0048178 A1* | 2/2015 | Edwards | G06F 3/011 239/128 |
| 2015/0222846 A1 | 8/2015 | Watson | |
| 2016/0301972 A1* | 10/2016 | Liu | H04N 21/4722 |
| 2017/0052748 A1* | 2/2017 | Dominique | G06F 3/147 |

* cited by examiner

AUDIO-EFFECT-ACTIVATED SCENT GENERATION METHOD AND SYSTEM

FIELD OF THE INVENTION

The present invention relates to a method and a system for generating a time-varying scent according to audio-meaningful events in an audio signal.

BACKGROUND

When a person is listening to a story in an audio programme broadcast through a FM radio, his or her user experience in enjoying the story can be greatly enhanced if the scent or odor in an ambient environment around the person is changeable and is time-coherently adapted to the context of the story. For example, when the audio programme produces a sound of gun firing, a smell of sulfur is introduced to the ambient environment.

In the art, techniques for synchronizing the playing of an audio file and the spreading of appropriate smell to an ambient environment in a coherent manner have been disclosed in US2015/0222846, US2013/0194437 and US2011/0268605. US2015/0222846 discloses a method of delivering and broadcasting aroma sensory information. The main idea is to encode an additional aroma "channel" into existing video and audio channels. An end user can smell the scent through a device activated by this additional channel. US2013/0194437 discloses a method of activating hear/feel/smell signals while a user is watching a video. The main idea is to use a mobile computing device to capture a predefined data-carrying pattern such as a QR code on the video screen. The mobile computing device decodes the pattern to obtain information to activate appropriate hear/feel/smell signals. US2011/0268605 discloses an apparatus having multiple scent releasing functions. The triggering of scent release is by computer control. One common characteristic among the techniques of US2015/0222846, US2013/0194437 and US2011/0268605 is that in each technique, additional information sent through an extra communication channel is required. It is disadvantageous in terms of the cost involved and the implementation difficulty.

Without an extra communication channel, timely release of appropriate smell in coherence with playing an audio file is possible by a technique of incorporating audio watermarks into the corresponding audio signal. However, a serious drawback is that the audio signal is required to be preprocessed before the user can play it. In practical situations, it is much more positive to user experience if the user can play any audio file acquired from anywhere and immediately enjoy the smell synchronized with excited moments according to the content of the audio file. The content resulting in excited moments exemplarily means meaningful events such as gun firing, glass breaking, door closing, car breaking, etc. Collectively, these meaningful events are referred to as "audio-meaningful events." These events are usually intended to create audio effects that impact end users. Desirably, filling the spaces around the end users with selected scents synchronized to the audio effects intensifies the impact.

It is desirable to have a technique of generating a time-varying scent according to audio-meaningful events in an audio signal without a need for side information carried in an extra communication channel to assist detecting and classifying the audio-meaningful events. Obviously, the user experience is significantly depressed if the generation of appropriate smell cannot follow the playing of the audio file. Hence, the technique is desired to be computationally simple for facilitating practical implementations. There is a need in the art to have such computationally simple technique.

SUMMARY OF THE INVENTION

A first aspect of the present invention is to provide a method for generating a time-varying scent according to audio-meaningful events appeared in an audio signal.

The method comprises the steps of: (a) extracting a fingerprint of the audio signal over a time window, wherein the fingerprint comprises a plurality of feature points; (b) hashing the plurality of feature points to yield a hash code having a fixed length and a smaller size than the plurality of feature points; (c) repeating the steps (a) and (b) for a sequence of consecutive time windows to obtain a plurality of hash codes; (d) providing a database comprising a plurality of entries, an individual entry comprising a predetermined hash-code segment and a scent-generating recipe, the predetermined hash-code segment being computed for a known audio-meaningful event, the scent-generating recipe including a list of at least one scent-generating substance for generating the scent upon detection of the known audio-meaningful event in the audio signal; (e) identifying, among all known audio-meaningful events associated with the plurality of entries, a matched audio-meaningful event such that a correlation between the plurality of hash codes and the predetermined hash-code segment computed for the matched audio-meaningful event is highest and exceeds a predetermined threshold correlation; and (f) when the matched audio-meaningful event is identified in the step (e), releasing each scent-generating substance in the list associated with the matched audio-meaningful event to generate the scent in response to appearance of the matched audio-meaningful event in the audio signal.

Optionally, the method further comprises the step (g) of repeating the steps (c), (e) and (f) for a next sequence of consecutive time windows until the audio signal ends. It is also optional that the method further comprises the step (h) of when the matched audio-meaningful event is not identifiable in the step (e), storing the plurality of hash codes and the audio signal spanned over the sequence of consecutive time windows for updating the database.

In the method, the correlation between the plurality of hash codes and the predetermined hash-code segment computed for an individual known audio-meaningful event may be computed as a number of hits. One hit is obtained when an individual hash code in the plurality of hash codes matches one hash code in the aforementioned predetermined hash-code segment.

In the step (a), preferably, the fingerprint is extracted from spectrogram data within the time window, where the spectrogram data are data of a spectrogram of the audio signal. It is preferable that the spectrogram is computed by taking a short-time Fourier transform (STFT) on the audio signal. The method may further include the step (i) of computing the spectrogram by taking the STFT on the audio signal.

It is also preferable that the method further comprises the step (j) of bandpass filtering the spectrogram for reducing noise, and thresholding the filtered spectrogram to remove a background thereof while retaining peaks, whereby the spectrogram obtained after both filtering and thresholding is used in the step (a).

In the step (a), the plurality of feature points may be obtained by including local maximum points, local minimum points, centroids, distance, time or any other measurable quantity as derived from the data of the spectrogram.

In one embodiment of the step (b), the hash code is computed from the plurality of feature points by SHA256.

A second aspect of the present invention is to provide a system for generating a time-varying scent according to audio-meaningful events appeared in an audio signal.

The system comprises one or more atomizers and one or more computing processors. An individual atomizer is used for selectively vaporizing an individual scent-generating substance. Thereby, one or more scent-generating substances are allowed to be selectively released for generating the time-varying scent. The one or more computing processors are configured to execute a process of generating the time-varying scent. The generating process comprises the steps of: (a) extracting a fingerprint of the audio signal over a time window, wherein the fingerprint comprises a plurality of feature points; (b) hashing the plurality of feature points to yield a hash code having a fixed length and a smaller size than the plurality of feature points; (c) repeating the steps (a) and (b) for a sequence of consecutive time windows to obtain a plurality of hash codes; (d) accessing a database that comprises a plurality of entries for retrieving the plurality of entries, an individual entry comprising a predetermined hash-code segment and a scent-generating recipe, the predetermined hash-code segment being computed for a known audio-meaningful event, the scent-generating recipe including a list of at least one scent-generating substance for generating the scent upon detection of the known audio-meaningful event in the audio signal; (e) identifying, among all known audio-meaningful events associated with the plurality of entries, a matched audio-meaningful event such that a correlation between the plurality of hash codes and the predetermined hash-code segment computed for the matched audio-meaningful event is highest and exceeds a predetermined threshold correlation; and (f) when the matched audio-meaningful event is identified in the step (e), configuring the one or more atomizers to release each scent-generating substance in the list associated with the matched audio-meaningful event to generate the scent in response to appearance of the matched audio-meaningful event in the audio signal.

Optionally, the generating process further comprises the step (g) of repeating the steps (c), (e) and (f) for a next sequence of consecutive time windows until the audio signal ends.

In the generating process, the correlation between the plurality of hash codes and the predetermined hash-code segment computed for an individual known audio-meaningful event may be computed as a number of hits. One hit is obtained when an individual hash code in the plurality of hash codes matches one hash code in the aforementioned predetermined hash-code segment.

In the step (a), preferably, the fingerprint is extracted from spectrogram data within the time window, where the spectrogram data are data of a spectrogram of the audio signal. It is preferable that the spectrogram is computed by taking a STFT on the audio signal. The generating process may further include the step (i) of computing the spectrogram by taking the STFT on the audio signal.

It is also preferable that the generating process further comprises the step (j) of bandpass filtering the spectrogram for reducing noise, and thresholding the filtered spectrogram to remove a background thereof while retaining peaks, whereby the spectrogram obtained after both filtering and thresholding is used in the step (a).

In the step (a), the plurality of feature points may be obtained by including local maximum points, local minimum points, centroids, distance, time or any other measurable quantity as derived from the data of the spectrogram.

In one embodiment of the step (b), the hash code is computed from the plurality of feature points by SHA256.

The system may further comprise one or more communication transceivers for enabling the one or more computing processors to communicate with entities external to the system. The one or more communication transceivers may be configured to communicate with the database via the Internet for enabling the one or more computing processors to retrieve the plurality of entries. The one or more communication transceivers may also be configured to communicate with a mobile computing device for retrieving the audio signal or accessing the database.

The system may be realized as one standalone device by at least integrating the one or more atomizers, the one or more computing processors and the one or more communication transceivers into the standalone device.

Other aspects of the present invention are disclosed as illustrated by the embodiments hereinafter.

DETAILED DESCRIPTION

The following definitions are used herein in the specification and appended claims. "A cloud" is construed and interpreted in the sense of cloud computing or, synonymously, distributed computing over a network unless otherwise specified. "A database" means an organized collection of data. The data of the database may be stored in one or more physical storages, or may be stored in a distributed manner by distributing the data in the cloud. Specifically, "a distributed database" is a database that stores the data in a distributed manner. "An audio-meaningful event" appeared in a duration of sound signal is a meaningful event recognizable by a reasonable person when the person hears and interprets the sound signal, where the meaningful event is not occurrence of an audio watermark for embedding data in the sound signal. Examples of audio-meaningful events include gun firing, glass breaking, water flowing, piano playing, door closing, person screaming, dog barking, etc. "A hashing function" means a function used to map data of arbitrary size to data of a fixed size. "Hashing" a data sequence means applying a hashing function to the data sequence to obtain a hash code having a fixed length.

A first aspect of the present invention is to provide a method for generating a time-varying scent according to audio-meaningful events appeared in an audio signal. The time-varying scent is determined by the audio-meaningful events. The method determines the audio-meaningful events from fingerprints of the audio signal. In particular, the Inventors have found that hashing the fingerprints to get hash codes and then comparing the hash codes against a database of stored hash codes enables quick determination of the audio-meaningful events while reducing computation and storage requirements in implementing the disclosed method.

Figure 1:
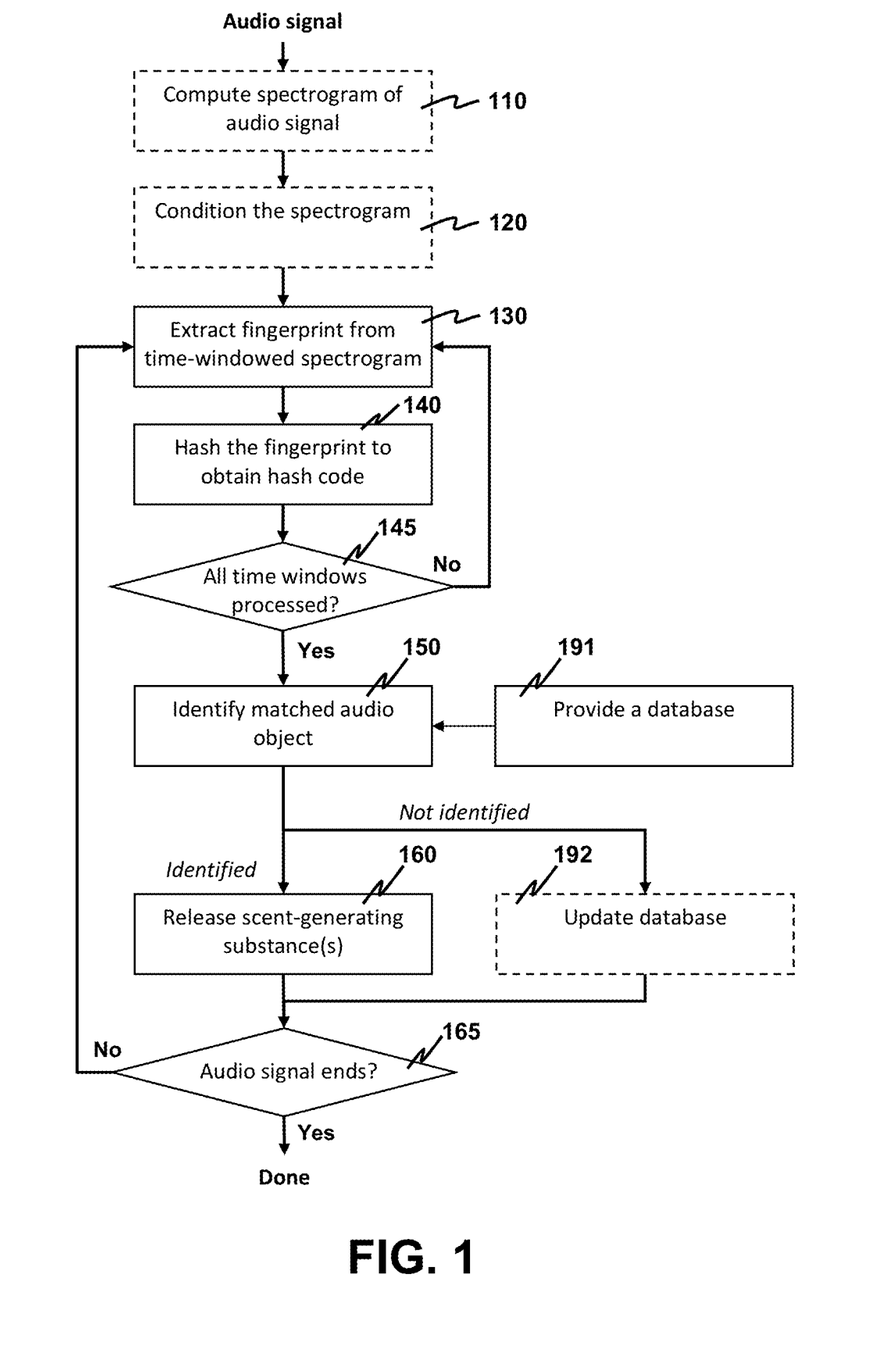
FIG. 1 depicts a flowchart showing steps of a method for generating time-varying scent in accordance with an exemplary embodiment of the present invention.

The method is illustrated with the aid of FIG. 1, which depicts a flowchart showing exemplary steps of the method.

To distinguish different audio-meaningful events, features of these events are required to be first identified. The feature of each such event is derivable through a fingerprint of the audio signal. In a step 130, the fingerprint is extracted from the audio signal over a certain predetermined time window. That is, a time segment of the audio signal rather than the entire audio signal is used to extract the fingerprint. The fingerprint comprises a plurality of feature points. Each feature point may be a certain quantifiable property of the audio signal, e.g., a signal power level of the audio signal over a pre-selected frequency band. Repeated application of the step 130 (as controlled by a step 145) yields a plurality of fingerprints over a consecutive sequence of time windows. As will be shown later, the plurality of fingerprints enables determination of the presence and the type of any audio-meaningful event in the audio signal.

The fingerprint may be obtained from time-domain processing the audio signal. For instance, U.S. Pat. No. 6,453, 252 reports one approach of determining a fingerprint that comprises subband energy levels of the audio signal by time-domain bandpass filtering the audio signal to obtain each subband signal followed by downsampling and calculating the subband energy level. Alternatively, since different audio-meaningful events are generally distinguishable in the transform domain, it is preferable to obtain the fingerprint in the step 130 by first projecting the audio signal into the transform domain and then extracting the fingerprint from data representing the audio signal in the transformed domain.

Since the audio signal of practical interest is not a stationary signal, the transform domain is advantageously and preferably selected to be a time-frequency domain. In one embodiment, the audio signal is processed by a time-frequency transform to generate a spectrogram (step 110). The spectrogram is a time-varying frequency-domain characterization of the audio signal. Hence, in the step 130, the fingerprint of the audio signal is extracted from spectrogram data obtained within the above-mentioned predetermined time window, where the spectrogram data means data of the spectrogram of the audio signal. As mentioned above, the fingerprint comprises the plurality of feature points. Each feature point may be a local maximum point, local minimum point, centroid, distance, time or any other measurable quantity as derived from the spectrogram data.

Figure 2:
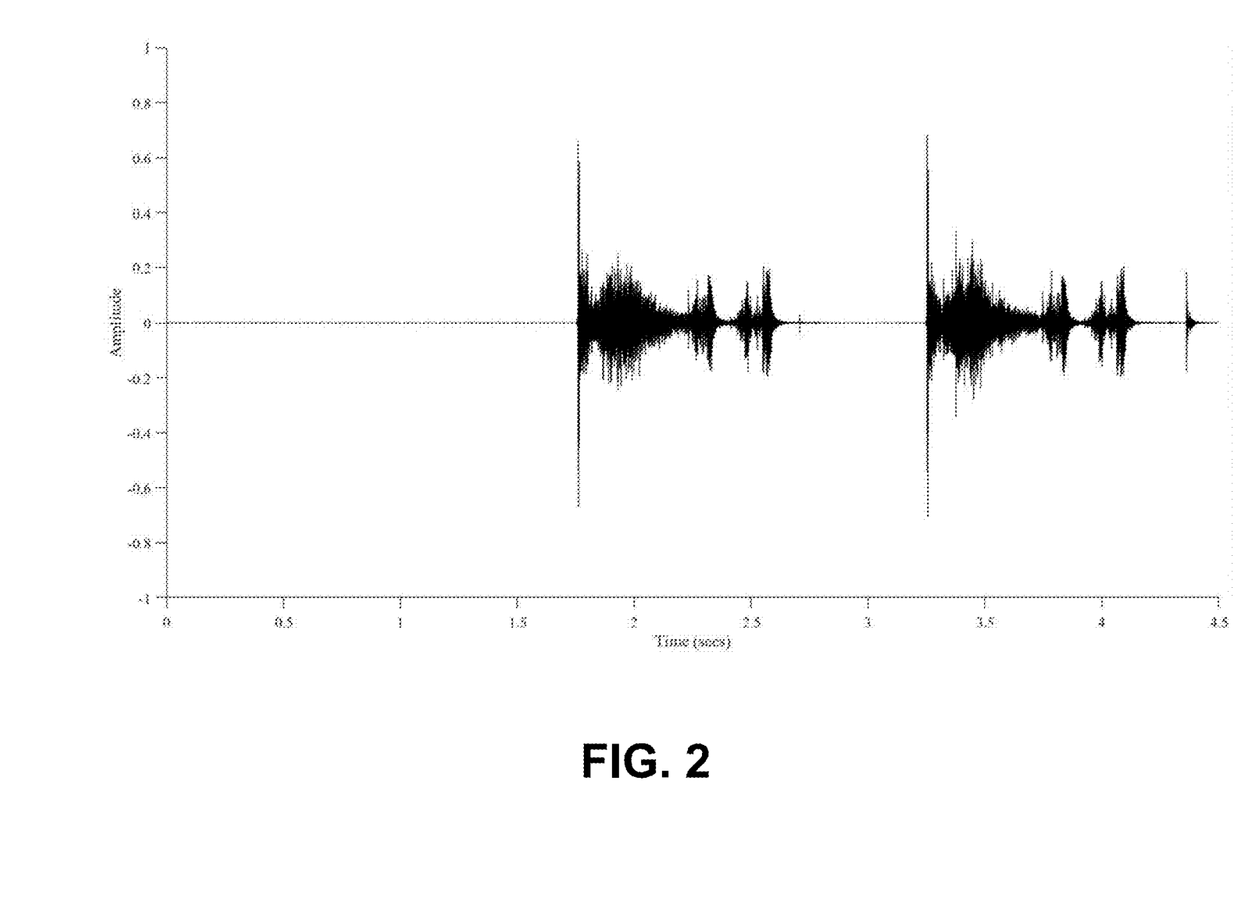
FIG. 2 depicts a sample of audio signal as an example for illustration.
Figure 3:
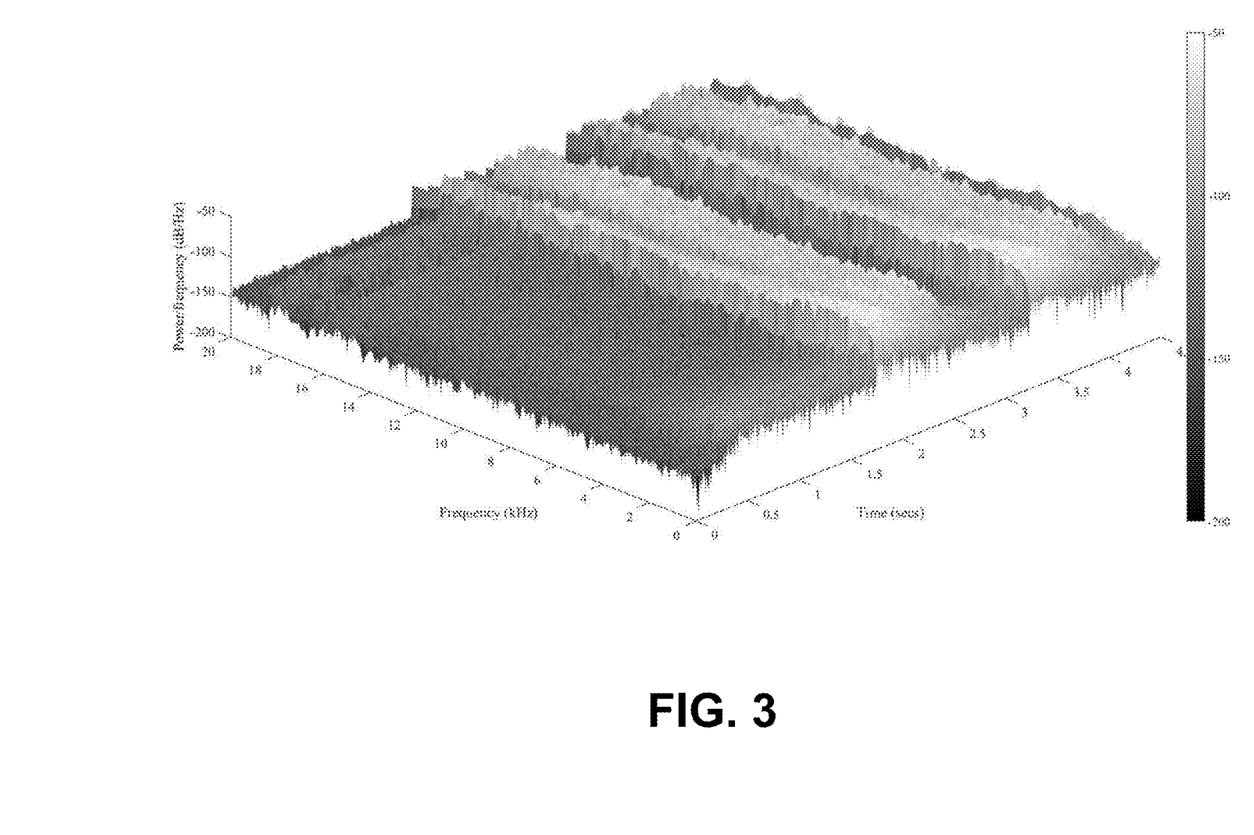
FIG. 3 depicts a spectrogram generated by applying a STFT to the audio signal sample of FIG. 2.

Preferably, the time-frequency transform is a STFT due to various advantages such as the ability of supporting parallel computation and the pipeline generation of STFT results without a need to wait for a complete audio signal to be available. Parallel execution of the steps 110 and 130 is thus realizable. Another advantage of using the STFT is that an audio-meaningful event of interest (such as gun firing) is usually short in time (<1 s) such that the frequency information of the audio signal can be quickly revealed. Other time-frequency transforms, such as wavelet transform, may also be used. As an example for illustration, FIG. 2 depicts a sample of audio signal and the audio signal sample is transformed by STFT into a spectrogram visually shown as a three-dimensional (3D) plot in FIG. 3.

Figure 4:
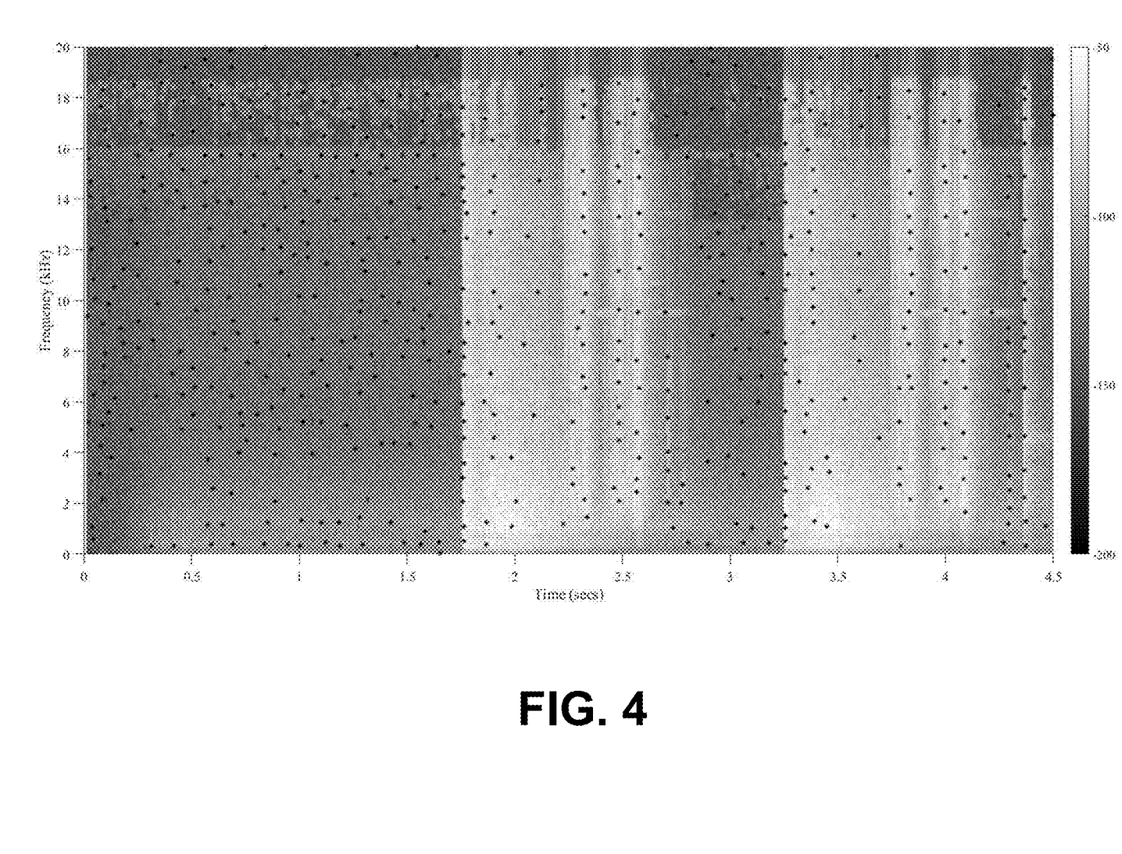
FIG. 4 depicts a filtered spectrogram obtained after bandpass filtering the spectrogram of FIG. 3.
Figure 5:
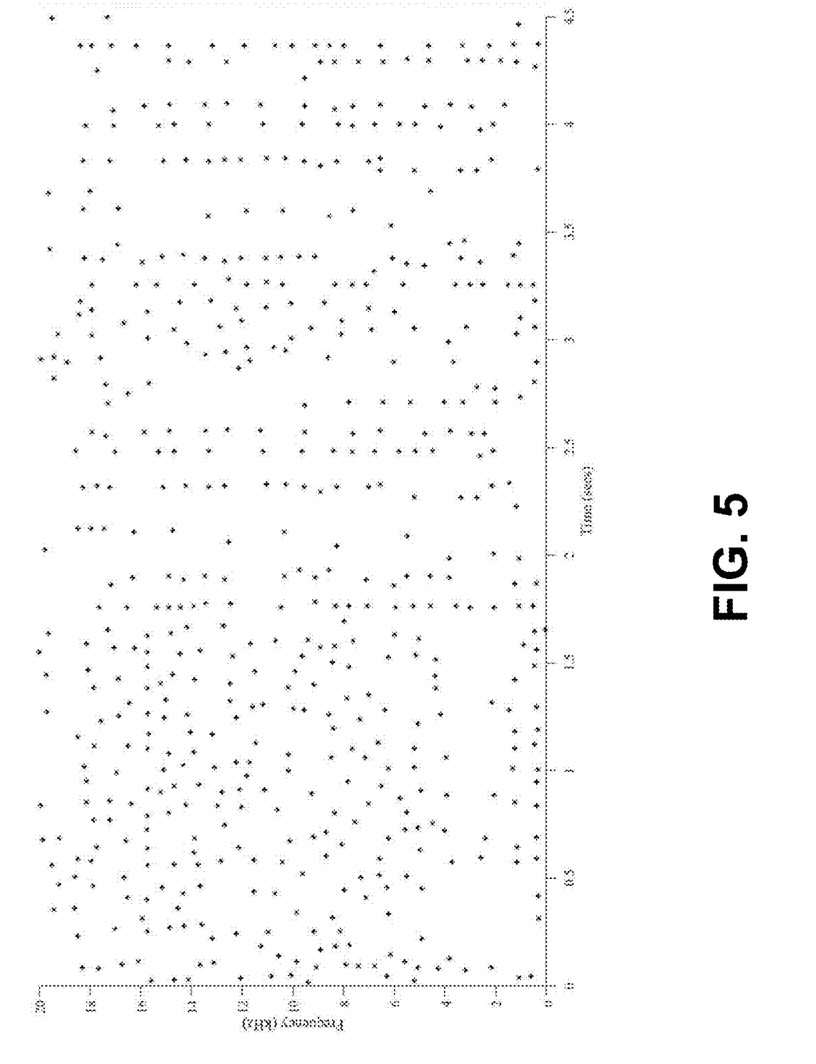
FIG. 5 depicts the result of removing the background by thresholding the filtered spectrogram of FIG. 4, leaving only the peaks.

Extraction of the plurality of feature points in the step 130 may not be easy as the spectrogram generated in the step 110 is usually not smooth and is often corrupted by noise. As an example, it is not easy to identify local minima or local maxima from the spectrogram of FIG. 3. Preferably, the spectrogram generated in the step 110 is conditioned (or filtered) before the fingerprint is extracted in the step 130. In a preferred step 120, the spectrogram is conditioned. In particular, the spectrogram is bandpass filtered to reduce noise, and thresholding of the filtered spectrogram follows in order to remove a background while retaining peaks (as illustrated in FIGS. 4 and 5). The spectrogram obtained after both filtering and thresholding is used for fingerprint extraction in the step 130. FIG. 4 depicts a filtered spectrogram obtained after bandpass filtering the spectrogram of FIG. 3. Peaks present in the filtered spectrogram are also shown in FIG. 4. These peaks are to be extracted to derive feature points in the step 130. This extraction is simplified if the background of the filtered spectrogram is removed. FIG. 5 shows the result of removing the background by thresholding the filtered spectrogram, leaving only a plurality of peaks.

Those skilled in the art will appreciate that if the STFT is used in the step 110, parallel execution of the steps 110, 120 and 130 is realizable by using appropriate parallel-computation techniques available in the art.

Figure 6:
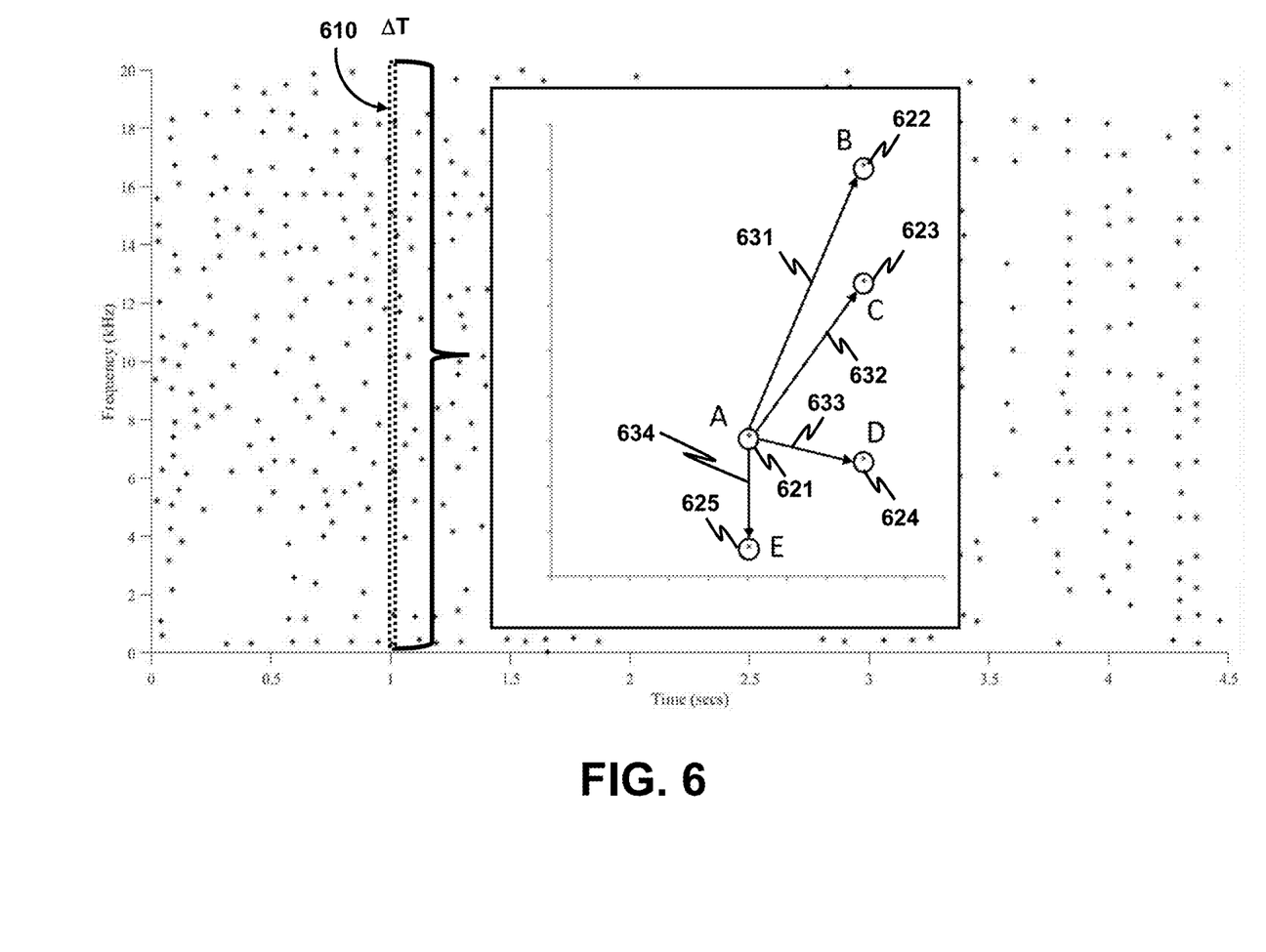
FIG. 6 illustrates, in accordance with one embodiment of the present invention, extracting feature points from the peaks shown in FIG. 5.

One embodiment of the step 130 is illustrated with reference to FIG. 6, which depicts extracting a plurality of feature points from the plurality of peaks of FIG. 5. First, a time window 610 within which the peaks (data of the spectrogram) are considered for feature point extraction is determined. The time window 610 has a length ΔT. Within the time window 610, there are five peaks identified: point A 621; point B 622; point C 623; point D 624; and point E 625. These five points 621-625 are used to derive the plurality of feature points consisting of (1) the time-frequency positions of the two points in each of point pairs AB 631, AC 632, AD 633 and AE 634, and (2) the distance of each of the aforementioned point pairs. The plurality of feature points forms the fingerprint.

Advantageously, the method includes a step 140 of hashing the plurality of feature points obtained in the step 130 to yield a hash code. The hash code has a fixed size and is smaller in size (number of data) than the plurality of feature points. Hashing is commonly used in data-security applications. In the present invention, the property of yielding fixed-size hash codes is advantageously utilized to reduce computation requirements in audio-meaningful event identification. Commonly available hashing functions may be used to generate the hash code from the plurality of feature points. In one embodiment, "SHA256", a published hashing function known in the field of data security, is used. For details of SHA256, see "US Secure Hash Algorithms (SHA and SHA-based HMAC and HKDF)," RFC 6234, Internet Engineering Task Force (IETF), May 2011. Consider FIG. 6 again for illustrating the step 140. The plurality of features points is inputted to the hashing function "SHA256" to obtain the hash code.

The steps 130 and 140 are repeated for a sequence of consecutive time windows (as controlled by the step 145). As a result, a plurality of hash codes is obtained. In the example shown in FIG. 6, the sequence of consecutive time windows is formed by sliding the time window 610 along the time axis.

In a real application, the steps 130 and 140 are looped for a fixed period of time, e.g., tenth of milliseconds for an audio effect having a duration of less than 1s. The hash codes collected within one loop may not be the whole set of hash codes for a particular audio-meaningful event. Here is an example. A gun shot, which lasts for 0.8 s, contains 1000 hash codes. If the loop is designed to be run with 50 ms, there will be less than 1000 hash codes collected each time. In other words, a partial set of hash codes is received. Therefore, one may identify which audio-meaningful event is present by comparing the partial hash-code set to those stored hash codes for different audio-meaningful events. Thus, one can predict an incoming audio-meaningful event without having the whole set of hash codes. It offers advantages of reduced computation requirements and reduced storage requirements. Furthermore and very importantly, it allows a fast and easy look-up and comparison to determine and identify the audio-meaningful event. The above-disclosed approach can give a fast recognition, which is practically important for real-time response to generate the appropriate time-varying scent.

In the disclosed method, a database containing hash-code segments for known audio-meaningful events is required in examining the plurality of hash codes generated by looping the steps 130, 140, 145. As used herein, "a hash-code segment" is a partial set of hash codes for comparison with the plurality of hash codes generated in the repeated execution of the steps 130 and 140. In a step 191, this database is provided and is made available. Those skilled in the art will appreciate that depending on practical situations, different approaches of providing (or accessing) the database are possible. This aspect will be further elaborated later. The database comprises a plurality of entries. Each entry includes a predetermined hash-code segment and a scent-generating recipe. The predetermined hash-code segment is computed for a known audio-meaningful event (namely, an audio-meaningful event that is already known in the preparation of the database). The scent-generating recipe includes a list of one or more scent-generating substances used for generating the scent when the aforesaid known audio-meaningful event is detected present in the audio signal. Those skilled in the art will be capable to identify suitable scent-generating substances, e.g., essential oils, to generate desired scents.

The advantage of hashing the fingerprint in the step 140 is apparent in reducing the storage requirement of the database. Since the hash code has a smaller size than the corresponding fingerprint, storing the predetermined hash-code segment for a known audio-meaningful event requires a smaller storage space than storing the corresponding fingerprint counterpart does. If the database is implemented in an end-user device, the device is simpler to be implemented. If the database is required to be transmitted to the end-user device via the Internet, the data-communication requirement is reduced.

The plurality of hash codes obtained in repeated execution of the step 140 is checked against the predetermined hash-code segments stored in the database to identify any possible audio-meaningful event present in the audio signal over a time duration of the sequence of consecutive time windows. If a certain known audio-meaningful event is present in the audio signal during the above-mentioned time duration, ideally the plurality of hash codes will match the corresponding predetermined hash-code segment. Correlating the plurality of hash codes with this predetermined hash-code segment will yield a correlation result indicating how much overlapping is obtained. Hence, a maximum-likelihood estimate of which audio-meaningful event is present is obtained by identifying a particular known audio-meaningful event (conveniently referred to as a matched audio-meaningful event) having a highest correlation result among all the known audio-meaningful events associated with the database. It is possible that no audio-meaningful event is actually present. In this particular case, the matched audio-meaningful event that is identified should be rejected. The rejection decision can be conveniently made when the correlation result associated with the matched audio-meaningful event is lower than a predetermined threshold correlation. Since hashing possesses strong collision resistance, the correlation result in an absence of audio-meaningful event is usually close to zero. Hence, the threshold correlation may be set to be a value close to zero. As a convenient choice, the threshold correlation may be set as ½ or ¼ of an expected maximum correlation value. As a summary, in a step 150, a matched audio-meaningful event is identified among all known audio-meaningful events associated with the plurality of entries of the database such that a correlation between the plurality of hash codes and the predetermined hash-code segment computed for the matched audio-meaningful event is highest and exceeds a predetermined threshold correlation.

Computation of the correlation can be done by a known formula in the art. Since each hash code is a digital word, one may simplify estimation the correlation by a compare-and-add procedure. If an individual hash code in the plurality of hash codes matches one hash code in the aforementioned predetermined hash-code segment, a "hit" is obtained. The correlation is then given by the number of hits. The matched audio-meaningful event is identified by having a highest number of hits among all the known audio-meaningful events.

The advantage of hashing the fingerprint in the step 140 is apparent in reducing the computation requirement in calculating the correlation since the hash code has a smaller size than the corresponding fingerprint.

After the step 150 is performed, two results are possible. One is that the matched audio-meaningful event is identified, and another one is not. If the matched audio-meaningful event is identified, each scent-generating substance in the list associated with the matched audio-meaningful event is released so as to generate the scent as a response to appearance of the matched audio-meaningful event in the audio signal (step 160). If the matched audio-meaningful event is not identifiable in the step 150, it implies that no audio-meaningful event is present or there is a new audio-meaningful event not yet known. No action may be done. Alternatively, the plurality of hash codes and the audio signal spanned over the sequence of consecutive time windows may be stored. In case a new type of audio-meaningful event associated with the plurality of hash codes is discovered, the database may be updated (step 192).

After the steps 150 and 160 are performed for the spectrogram over the sequence of consecutive time windows, the steps 130, 140, 145, 150 and 160 are repeated for a next sequence of consecutive time windows usually until the audio signal ends (as controlled by a step 165).

A second aspect of the present invention is to provide a system for generating a time-varying scent according to audio-meaningful events appeared in an audio signal, where the scent is generated according to any embodiment of the method disclosed above in the first aspect of the present invention.

Figure 7:
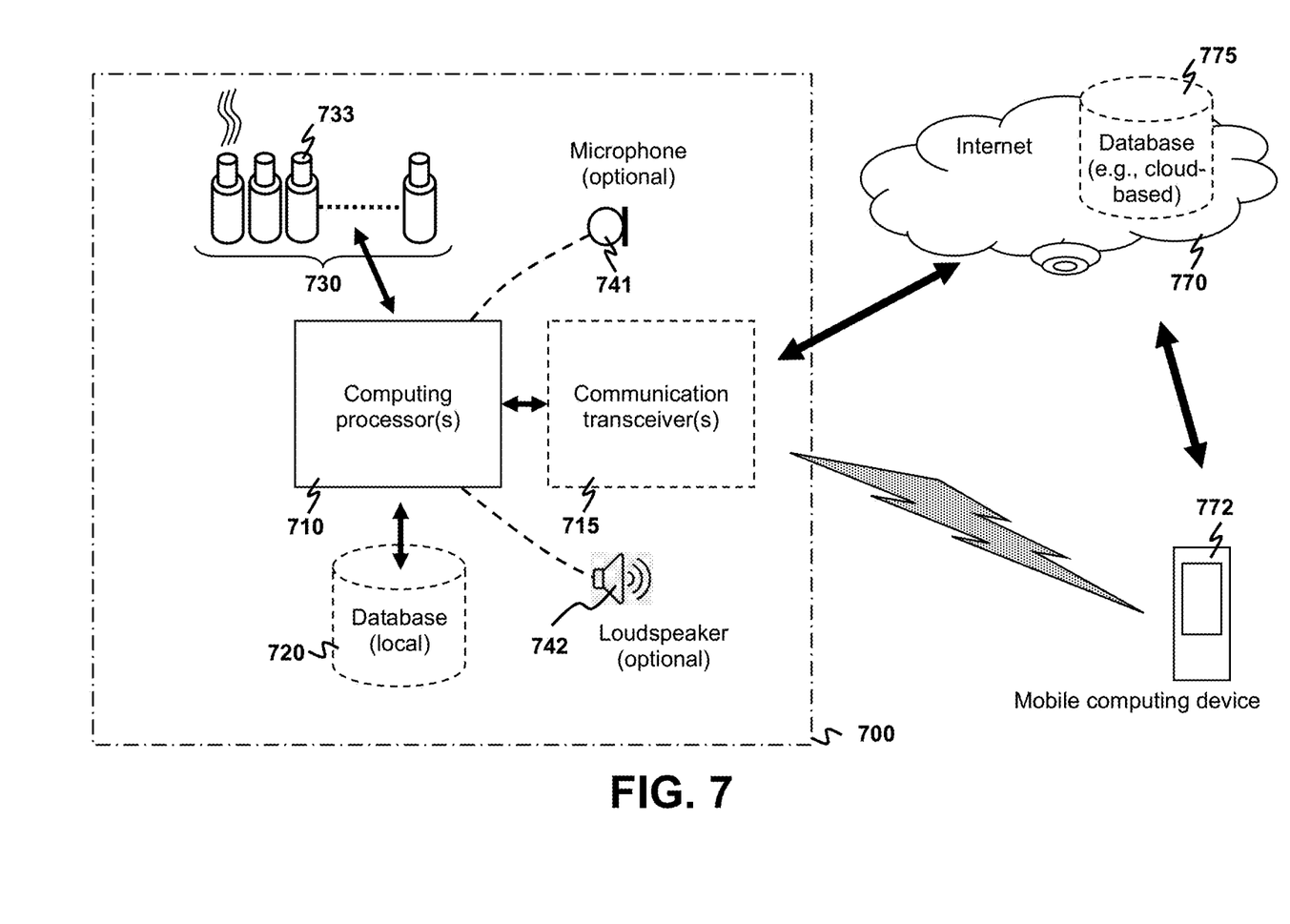
FIG. 7 depicts a system for generating time-varying scent in accordance with an exemplary embodiment of the present invention.

The system is exemplarily explained with reference to FIG. 7. In FIG. 7, a system 700 for generating time-varying scent in accordance with an exemplary embodiment of the present invention is shown.

The system 700 comprises one or more atomizers 730 and one or more computing processors 710. An individual atomizer (e.g., atomizer 733), which is controllable by the one or more computing processors 710, is used for selectively vaporizing an individual scent-generating substance. Hence, the one or more atomizers 730 allow one or more scent-generating substances to be selectively released for generating the time-varying scent. The one or more computing processors 710 are configured to generate the time-varying scent at least via activating the one or more atomizers 730. Exemplarily, the one or more computing processors 710 are configured to execute the steps 110, 120, 130, 140, 145, 150 and 165, and to configure or control the one or more atomizers 730 to execute the step 160 when the one or more computing processors 710 identify the matched audio-meaningful event in the step 150. The one or more computing processors 710 are also arranged to access the database that is mentioned in the step 191.

In some applications, the database may be a local database 720 residing in the system 700. In some other applications, the database may reside in the Internet 770. This database (referenced by 775) may be a standalone database or a distributed database.

To enable the one or more computing processors 710 to access the database 775, one or more communication transceivers 715 for enabling the one or more computing processors 710 to communicate with entities external to the system 700 are included in the system 700 and coupled to the one or more computing processors 710. The one or more communication transceivers 715 may provide a wired connection to the Internet 770 such as an Ethernet connection, or a wireless connection such as WiFi. The one or more communication transceivers 715 may also access the Internet 770 to reach the database 775 via a mobile computing device 772. For example, the one or more communication transceivers 715 provide Bluetooth wireless connectivity, or USB wired connectivity, with the mobile computing device 772.

It is also possible that the one or more communication transceivers 715 enable the one or more computing processors 710 to download the audio signal from the Internet 770 or from the mobile computing device 772.

The system 700 may further include a loudspeaker 742 to convert the audio signal into sound for human consumption.

Alternatively, the audio signal may be obtained from environmental sound around the system 700. When a user wishes to enjoy surrounding scent to be "linked" to the environmental sound, the system 700 may use a microphone 741 to capture the environmental sound and convert it into the audio signal, which is then used to guide the system 700 to generate the time-varying scent. In another option, the audio signal may be obtained from any audio-signal generating device, such as the mobile computing device 772, a desktop computer, a television, a movie player, a home-entertainment center, etc., by wired or wireless connection.

The system 700 may be realized as one standalone device by at least integrating the one or more atomizers 730, the one or more computing processors 710 and the one or more communication transceivers 715 into the standalone device. The standalone device may further include the loudspeaker 742 and/or the microphone 741. In one practical example, the standalone device is shaped and formed as a headset with the functionalities of producing sound from an audio signal and generating a time-varying scent according to the content of the audio file. Those skilled in the art may refer to, e.g., U.S. Pat. No. 8,295,529 for information on incorporating atomizers into a headset for vaporizing scent-generating chemicals. Those skilled in the art may refer to, e.g., U.S. Pat. No. 9,669,364 for details on atomizers suitable for vaporizing common scent-generating substances such as essential oils.

Obviously, the above-disclosed embodiments of the present invention are merely examples for clearly illustrating the present invention, rather than limiting the present invention. For those skilled in the art, other variations or changes may be made on the basis of the above description. There is no need and no exhaustion for all of the embodiments. Any modification, equivalent replacement and improvement made within the spirit and principle of the present invention should be included in the protection scope of the appended claims of the present invention.

What is claimed is:

1. A method for generating a time-varying scent according to audio-meaningful events appeared in an audio signal, the method comprising the steps of:
   (a) extracting a fingerprint of the audio signal over a time window, wherein the fingerprint comprises a plurality of feature points;
   (b) hashing the plurality of feature points to yield a hash code, wherein the hash code has a fixed length and a smaller size than the plurality of feature points;
   (c) repeating the steps (a) and (b) for a sequence of consecutive time windows to obtain a plurality of hash codes;
   (d) providing a database comprising a plurality of entries, an individual entry comprising a predetermined hash-code segment and a scent-generating recipe, the predetermined hash-code segment being computed for a known audio-meaningful event, the scent-generating recipe including a list of at least one scent-generating substance for generating the scent upon detection of the known audio-meaningful event in the audio signal;
   (e) identifying, among all known audio-meaningful events associated with the plurality of entries, a matched audio-meaningful event such that a correlation between the plurality of hash codes and the predetermined hash-code segment computed for the matched audio-meaningful event is highest and exceeds a predetermined threshold correlation;
   (f) when the matched audio-meaningful event is identified in the step (e), releasing each scent-generating substance in the list associated with the matched audio-meaningful event to generate the scent in response to appearance of the matched audio-meaningful event in the audio signal; and
   (g) repeating the steps (c), (e) and (f) for a next sequence of consecutive time windows until the audio signal ends.

2. The method of claim 1, wherein in the step (a), the fingerprint is extracted from spectrogram data within the time window, the spectrogram data being data of a spectrogram of the audio signal.

3. The method of claim 2 further comprising the step of:
   (i) computing the spectrogram by taking a short-time Fourier transform (STFT) on the audio signal.

4. The method of claim 2 further comprising the step of:
   (j) bandpass filtering the spectrogram for reducing noise, and thresholding the filtered spectrogram to remove a background thereof while retaining peaks, whereby the spectrogram obtained after both filtering and thresholding is used in the step (a).

5. The method of claim 2, wherein in the step (a), the plurality of feature points is obtained by including local maximum points, local minimum points, centroids, distance, time or any other measurable quantity as derived from the spectrogram data.

6. The method of claim 1, wherein the correlation between the plurality of hash codes and the predetermined hash-code segment computed for an individual known audio-meaningful event is computed as a number of hits, one hit being obtained when an individual hash code in the plurality of hash codes matches one hash code in the aforementioned predetermined hash-code segment.

7. The method of claim 1 further comprising the step of:
(h) when the matched audio-meaningful event is not identifiable in the step (e), storing the plurality of hash codes and the audio signal spanned over the sequence of consecutive time windows for updating the database.

8. The method of claim 1, wherein in the step (b), the hash code is computed from the plurality of feature points by SHA256.

9. A system for generating a time-varying scent according to audio-meaningful events appeared in an audio signal, the system comprising:
one or more atomizers each for selectively vaporizing an individual scent-generating substance to thereby allow one or more scent-generating substances to be selectively released for generating the time-varying scent; and
one or more computing processors configured to execute a process of generating the time-varying scent;
wherein the generating process comprises the steps of:
(a) extracting a fingerprint of the audio signal over a time window, wherein the fingerprint comprises a plurality of feature points;
(b) hashing the plurality of feature points to yield a hash code having a fixed length and a smaller size than the plurality of feature points;
(c) repeating the steps (a) and (b) for a sequence of consecutive time windows to obtain a plurality of hash codes;
(d) accessing a database that comprises a plurality of entries for retrieving the plurality of entries, an individual entry comprising a predetermined hash-code segment and a scent-generating recipe, the predetermined hash-code segment being computed for a known audio-meaningful event, the scent-generating recipe including a list of at least one scent-generating substance for generating the scent upon detection of the known audio-meaningful event in the audio signal;
(e) identifying, among all known audio-meaningful events associated with the plurality of entries, a matched audio-meaningful event such that a correlation between the plurality of hash codes and the predetermined hash-code segment computed for the matched audio-meaningful event is highest and exceeds a predetermined threshold correlation; and
(f) when the matched audio-meaningful event is identified in the step (e), configuring the one or more atomizers to release each scent-generating substance in the list associated with the matched audio-meaningful event to generate the scent in response to appearance of the matched audio-meaningful event in the audio signal.

10. The system of claim 9, wherein in the step (a), the fingerprint is extracted from spectrogram data within the time window, the spectrogram data being data of a spectrogram of the audio signal.

11. The system of claim 10, wherein the generating process further comprises the step of:
(i) computing the spectrogram by taking a short-time Fourier transform (STFT) on the audio signal.

12. The system of claim 9 further comprising:
one or more communication transceivers for enabling the one or more computing processors to communicate with entities external to the system.

13. The system of claim 12, wherein the one or more communication transceivers are configured to communicate with the database via the Internet for enabling the one or more computing processors to retrieve the plurality of entries.

14. The system of claim 12, wherein the one or more communication transceivers are configured to communicate with a mobile computing device for retrieving the audio signal or accessing the database.

15. The system of claim 12, wherein at least the one or more atomizers, the one or more computing processors and the one or more communication transceivers are integrated as one standalone device such that the system is realized as this device.

16. The system of claim 9, wherein the correlation between the plurality of hash codes and the predetermined hash-code segment computed for an individual known audio-meaningful event is computed as a number of hits, one hit being obtained when an individual hash code in the plurality of hash codes matches one hash code in the aforementioned predetermined hash-code segment.

17. The system of claim 9, wherein the generating process further comprises the step of:
(g) repeating the steps (c), (e) and (0 for a next sequence of consecutive time windows until the audio signal ends.

18. The system of claim 9, wherein in the step (b), the hash code is computed from the plurality of feature points by SHA256.

* * * * *